US00PP16096P2

(12) United States Plant Patent
Croon

(10) Patent No.: US PP16,096 P2
(45) Date of Patent: Nov. 8, 2005

(54) ***COREOPSIS* PLANT NAMED 'CREME BRULÉE'**

(50) Latin Name: *Coreopsis verticillata*
Varietal Denomination: Crème Brulée

(76) Inventor: June Croon, P.O. Box 28, Cutchogue, NY (US) 11935

( * ) Notice: Subject to any disclaimer, the term of this patent is extended or adjusted under 35 U.S.C. 154(b) by 0 days.

(21) Appl. No.: 10/917,145

(22) Filed: Aug. 12, 2004

(51) Int. Cl.[7] ..... A01H 5/00
(52) U.S. Cl. ..... Plt./263

(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Coreopsis* plant named 'Crème Brulée', characterized by its upright, outwardly spreading and mounded growth habit; very freely basal branching habit; narrow, lacy and bright green-colored foliage; very freely flowering habit with numerous inflorescences per plant; large daisy-type inflorescences; bright yellow-colored ray florets and darker yellow-colored disc florets; long flowering period; and relatively resistant to Powdery Mildew.

1 Drawing Sheet

Botanical classification/cultivar designation: *Coreopsis verticillata* cultivar Crème Brulée.

BACKGROUND OF THE INVENTION

The present invention relates to a new and distinct cultivar of *Coreopsis* plant, botanically known as *Coreopsis verticillata* and hereinafter referred to by the cultivar name 'Crème Brulée'.

The new *Coreopsis* was discovered and selected by the Inventor in a controlled environment in Mattituck, N.Y. in 1997, as a naturally-occurring whole plant mutation of the *Coreopsis verticillata* cultivar Moonbeam, not patented. The new *Coreopsis* was observed as a single plant in a group of flowering plants of the cultivar Moonbeam.

Asexual reproduction of the new *Coreopsis* by cuttings in a controlled environment in Mattituck, N.Y., since 1999, has shown that the unique features of this new *Coreopsis* are stable and reproduced true to type in successive generations.

SUMMARY OF THE INVENTION

The cultivar Crème Brulée has not been observed under all possible environmental conditions. The phenotype may vary somewhat with variations in environment such as temperature and light intensity, without, however, any variance in genotype.

The following traits have been repeatedly observed and are determined to be the unique characteristics of 'Crème Brulée'. These characteristics in combination distinguish 'Crème Brulée' as a new and distinct cultivar:

1. Upright, outwardly spreading and mounded growth habit.
2. Very freely basal branching habit.
3. Narrow, lacy and bright green-colored foliage.
4. Very freely flowering habit with numerous inflorescences per plant.
5. Large daisy-type inflorescences that are about 4.5 cm in diameter.
6. Bright yellow-colored ray florets and dark yellow-colored disc florets.

7. Long flowering period.
8. Relatively resistant to Powdery Mildew.

Plants of the new *Coreopsis* are most similar to plants of the parent, the cultivar Moonbeam. In side-by-side comparisons conducted in Mattituck, N.Y., plants of the new *Coreopsis* differed from plants of the cultivar Moonbeam in the following characteristics:

1. Plants of the new *Coreopsis* were more vigorous than plants of the cultivar Moonbeam.
2. Plants of the new *Coreopsis* had brighter green-colored foliage than plants of the cultivar Moonbeam.
3. Flowers of plants of the new *Coreopsis* were positioned at the plant canopy whereas flowers of plants of the cultivar Moonbeam were positioned above the plant canopy.
4. Plants of the new *Coreopsis* had larger inflorescences than plants of the cultivar Moonbeam.
5. Ray florets of plants of the new *Coreopsis* were darker yellow in color and had more emarginate apices than ray florets of plants of the cultivar Moonbeam.
6. Plants of the new *Coreopsis* were more resistant to Powdery Mildew than plants of the cultivar Moonbeam.

BRIEF DESCRIPTION OF THE PHOTOGRAPH

The accompanying colored photograph illustrates the overall appearance of the new *Coreopsis*, showing the colors as true as it is reasonably possible to obtain in colored reproductions of this type. Colors in the photograph may differ slightly from the color values cited in the detailed botanical description which accurately describe the colors of the new *Coreopsis*.

The photograph comprises a side perspective view of typical one-year old flowering plants of 'Crème Brulée' grown in the landscape in an outdoor nursery in Pennsylvania.

DETAILED BOTANICAL DESCRIPTION

In the following description, color references are made to The Royal Horticultural Society Colour Chart, 1995 Edition, except where general terms of ordinary dictionary significance are used. The following observations and measurements describe pinched plants grown in Tolar, Tex. during the summer in an outdoor nursery under full sun and cultural conditions which approximate commercial practice. Plants used for the photographs and descriptions were grown as single plants in one-gallen containers and were about six months old. Measurements and numerical values represent averages taken from a group of flowering plants.

Botanical classification: *Coreopsis verticillata* cultivar Crème Brulée.

Parentage: Naturally-occurring whole plant mutation of *Coreopsis verticillata* Moonbeam, not patented.

Propagation:

*Type*.—By cuttings.

*Time to initiate roots*.—Summer: About one week at temperatures of 23 to 29° C. Winter: About two weeks at temperatures of 15 to 20° C.

*Time to produce a rooted cutting*.—Summer: About five weeks at temperatures of 23 to 29° C. Winter: About six to seven weeks at temperatures of 15 to 20° C.

*Root description*.—Fine, fibrous and well-branched.

Plant description:

*Appearance*.—Perennial; upright and outwardly spreading; mounding plant habit. Flowers positioned at the plant canopy level.

*Plant height*.—About 34 cm.

*Plant diameter or spread*.—About 37 cm.

*Lateral branch description*.—Freely basal branching, usually two laterals will develop at every node. Pinching is not required, however plants tend to be sturdier and denser if pinched. Aspect: Initially upright, then outwardly spreading. Length: About 33 cm. Diameter: About 3 mm. Internode length: About 3.4 cm. Texture: Pubescent. Color: Close to 146A.

*Foliage description*.—Arrangement: Opposite, single; sessile. Length: About 8.5 cm. Width: About 1 cm. Shape: Narrowly lanceolate to tri-lobed and deeply dissected; lacy appearance. Apex: Acuminata. Base: Attenuate. Margin: Entire. Texture, upper and lower surfaces: Pubescent. Color: Developing and fully expanded foliage, upper surface: Brighter green than 147A; venation, similar to lamina. Developing and fully expanded foliage, lower surface: Close to 147B; venation, similar to lamina.

Flowering description:

*Appearance*.—Large daisy-type composite inflorescence form with elongated oblong-shaped ray florets. Inflorescences borne on terminals, arising from leaf axils. Disc and ray florets develop acropetally on a capitulum. Inflorescences persistent.

*Flowering response*.—Under natural conditions, plant flower during the summer and through the autumn in Northeastern Texas.

*Inflorescence longevity*.—Individual inflorescences last about one to two weeks.

*Quantity of inflorescences*.—Very freely flowering with more than 100 buds and inflorescences per plant.

*Inflorescence size*.—Diameter: About 4.5 cm; large. Depth (height): About 1.2 cm. Diameter of disc: About 7.5 mm.

*Fragrance*.—None detected.

*Inflorescence buds*.—Height: About 7 mm. Diameter: About 7 mm. Shape: Roughly spherical. Color: Close to 144A.

*Ray florets*.—Shape: Elongated oblong. Length: About 2.2 cm. Width: About 1.1 cm. Apex: Emarginate; deeply incised, jagged. Base: Attenuate; short corolla tube. Corolla tube length: About 3.5 mm. Margin: Entire. Texture: Smooth, glabrous; velvety. Aspect: Initially upright; when mature, about 90° from vertical, perpendicular to peduncle. Initially concave; when mature; mostly flat. Number of ray florets per inflorescence: About eight arranged in a single whorl. Color: When opening, upper and lower surfaces: Close to 7A to 9A. Fully opened, upper surface: Close to 7A. Fully opened, lower surface: Close to 6A.

*Disc florets*.—Arrangement: Massed at the center of the inflorescence. Shape: Tubular, flared at apex; five pointed apices. Length: About 7 mm. Width: Apex: About 1.5 mm. Base: About 1 mm. Number of disc florets per inflorescence: About 64. Color: Immature: Close to 154A. Mature: Towards the apex, close to 15A; towards the base, close to 154A.

*Involucral bracts*.—Quantity: About eight arranged in a single whorl. Length: About 5 mm. Width: About 3 mm at the base. Shape: Narrowly deltoid. Apex: Acute. Base: Truncate. Texture, upper and lower surfaces: Smooth, glabrous; waxy. Color, upper and lower surfaces: Close to 144A.

*Peduncle*.—Strength: Very strong, wiry; flexible. Aspect: Mostly upright. Length: About 5.5 cm. Diameter: About 1 mm. Texture: Smooth, glabrous. Color: Between 144A and 146A.

*Reproductive organs*.—Androecium: Present on disc florets only. Stamen quantity: Five per floret. Anther length: About 1 mm. Anther color: More brown than 187A. Amount of pollen: Moderate. Pollen color: 17A. Gynoecium: Present on disc florets only. Pistil quantity: One per floret. Pistil length: About 7.5 mm. Stigma shape: Bi-parted. Stigma color: Close to 9A to 12A. Style color: Close to 9A.

*Seed/fruit*.—Seed/fruit production has not been observed.

Disease/pest resistance: Compared to plants of other *Coreopsis* cultivars known to the Inventor, plants of the new *Coreopsis* have been observed to be more resistant to Powdery Mildew. Resistance to pests and other pathogens common to *Coreopsis* has not been observed on plants grown under commercial conditions.

Temperature tolerance: Plants of the new *Coreopsis* have demonstrated good tolerance to night temperatures as low as −20° C. and day temperatures as high as 42° C.

It is claimed:

1. A new and distinct cultivar of *Coreopsis* plant named 'Crème Brulée', as illustrated and described.

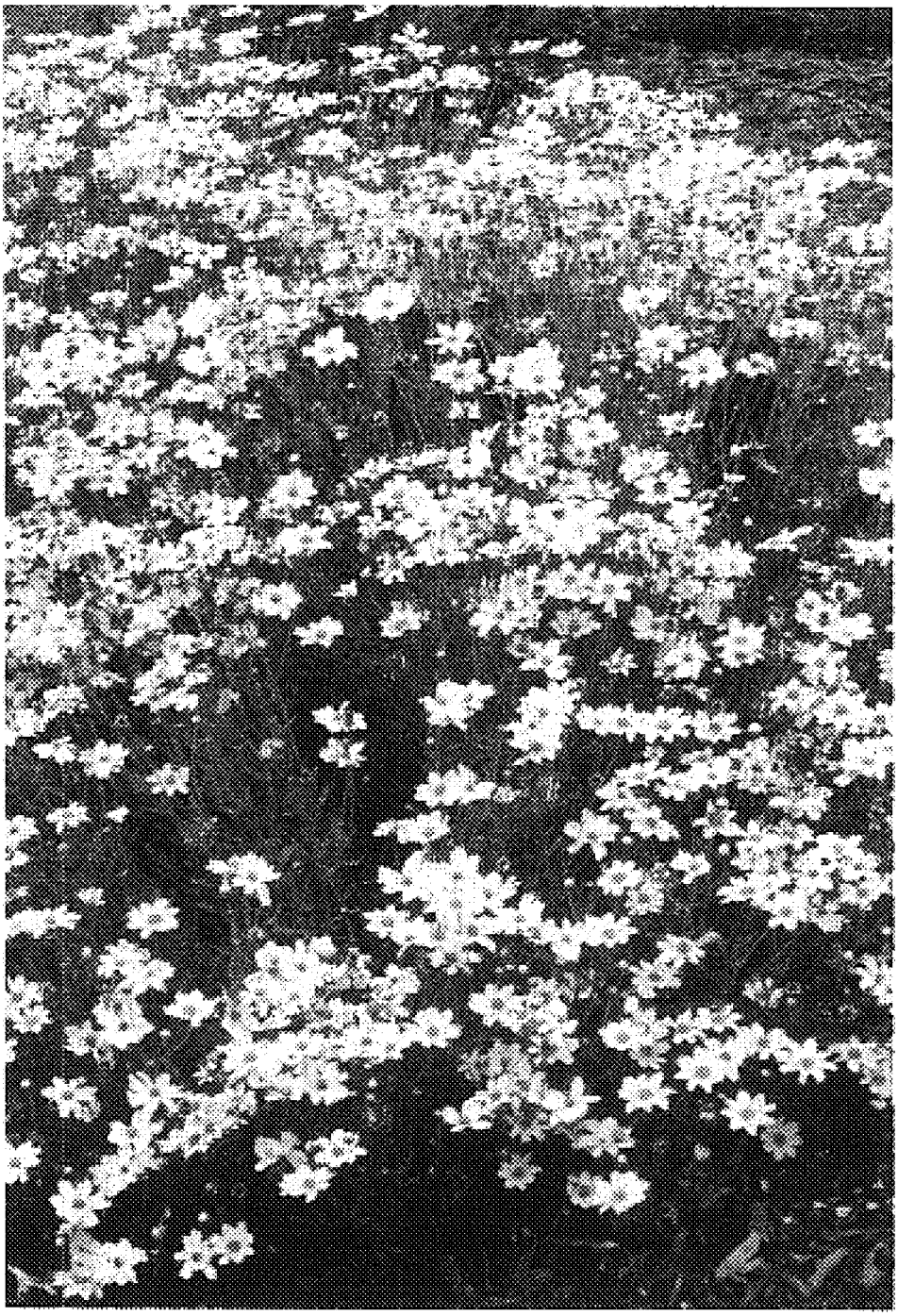

* * * * *